United States Patent [19]

Yoshikawa

[11] Patent Number: 5,441,945
[45] Date of Patent: Aug. 15, 1995

[54] HETEROCYCLIC IMINOBISMETHYLENEBISPHOSPHONIC ACID DERIVATIVES

[75] Inventor: Katsuhiro Yoshikawa, Kawagoe, Japan

[73] Assignee: Hoechst Japan Limited, Tokyo, Japan

[21] Appl. No.: 227,351

[22] Filed: Apr. 13, 1994

[30] Foreign Application Priority Data

Apr. 15, 1993 [JP] Japan .................... 5-087692

[51] Int. Cl.$^6$ .............. A61K 31/675; C07F 9/06; C07F 9/28
[52] U.S. Cl. ............................ 514/80; 514/89; 514/94; 546/22; 546/23; 548/112; 548/113; 548/119
[58] Field of Search ............... 546/22, 23; 548/112, 548/113, 119; 514/80, 89, 94

[56] References Cited

U.S. PATENT DOCUMENTS

| | | | |
|---|---|---|---|
| 3,674,804 | 7/1972 | Redmore | 546/112 |
| 4,687,767 | 8/1987 | Bosies et al. | 514/80 |
| 4,784,993 | 11/1988 | Bosies et al. | 514/80 |
| 4,917,737 | 4/1990 | Carey et al. | 148/250 |
| 4,929,606 | 5/1990 | Jaeggi | 514/80 |
| 5,002,937 | 3/1991 | Bosies et al. | 514/80 |
| 5,039,669 | 8/1991 | Isomura et al. | 514/80 |
| 5,057,505 | 10/1991 | Widler et al. | 514/80 |
| 5,190,930 | 3/1993 | Jaeggi | 514/94 |
| 5,280,022 | 1/1994 | Sohda et al. | 514/80 |
| 5,294,608 | 3/1994 | Lang et al. | 514/80 |

FOREIGN PATENT DOCUMENTS 0186405 12/1985 European Pat. Off. .
2185387 5/1973 France .
59-52805 3/1984 Japan .

OTHER PUBLICATIONS

Research Disclosure (RSDSBB 03744353), May 1979, Liszewski, L. J. et al., "Method To Prevent Precipitation Of Iron In Photographic Processor Effluents," vol., 181, p. 230.
English language abstract of FR 2185387.
English language abstract of JP 59-52805.

*Primary Examiner*—Cecilia Tsang
*Attorney, Agent, or Firm*—Finnegan, Henderson, Farabow, Garrett & Dunner

[57] ABSTRACT

The heterocyclic iminobismethylenebisphosphonic acid derivatives of the general formula (I)

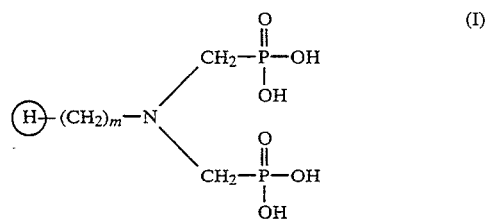

wherein n is an integer of 0-5 and the group of the formula

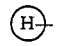

represents a 4-7 membered monocyclic or 7-11 membered condensed heterocyclic ring group which may be substituted by a halogen atom or a lower alkyl group and contains 1-2 nitrogen atoms their esters and salts thereof are described. The said compounds are useful as a bone resorption inhibitor, a dental calculus formation inhibitory agent or a polyvalent metal ion complex salt forming agent.

10 Claims, No Drawings

HETEROCYCLIC IMINOBISMETHYLENEBISPHOSPHONIC ACID DERIVATIVES

This invention relates to new heterocyclic iminobismethylenebisphosphonic acid derivatives. The compounds can be used as a bone resorption inhibitor, a dental calculus formation inhibitory agent and a polyvalent metal ion complex salt forming agent.

Although various compounds have so far been synthesized as iminobismethylenebisphosphonic acid derivatives, those having a hetero ring as disclosed in the present invention has not been known.

The present invention describes novel heterocyclic iminobismethylenebisphosphonic acid derivatives which are useful as a bone resorption inhibitor, a dental calculus formation inhibitory agent and a polyvalent metal ion complex salt forming agent.

The heterocyclic iminobismethylenebisphosphonic acid derivatives of this invention are the heterocyclic iminobismethylenebisphosphonic acid derivative of the general formula (I)

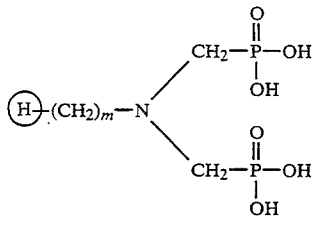

(I)

wherein
n is an integer of 0-5, and the group of the formula

represents a 4-7 membered monocyclic or 7-11 membered condensed heterocyclic group containing 1 or 2 nitrogen atoms which may be substituted by a halogen atom(s) or a lower alkyl group(s)), and esters or salts thereof.

The lower alkyl group as a substituent for the heterocyclic group is a straight or branched alkyl group having 1-6 carbon atoms, for preferable example, a methyl group, an ethyl group, a propyl group, an isopropyl group, a butyl group, an isobutyl group and a t-butyl group. For preferable example of the halogen atom as a substituent, there may be fluorine, chlorine, and bromine.

Preferred embodiments of the present invention are the heterocyclic iminobismethylenebisphosphonic acid derivatives of the general formula (I) wherein the group of the formula

is represented by the formula

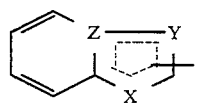

wherein Z, Y and X are individually a carbon atom or a nitrogen atom, and ═══════ is a double bond or a single bond, and wherein the group of the formula

is represented by a pyridyl group, a pyrazyl group, an imidazolyl group, a pyrrolyl group, a pyrazolyl group or a pyrimidyl group.

Moreover, the preferable bisphosphonic acid derivatives are those compounds represented by the following formulae

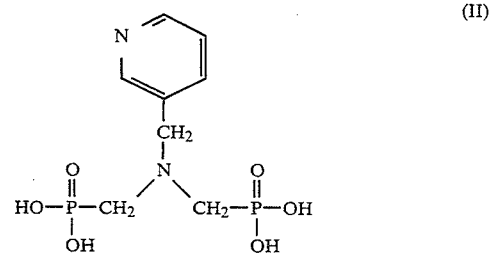

(II)

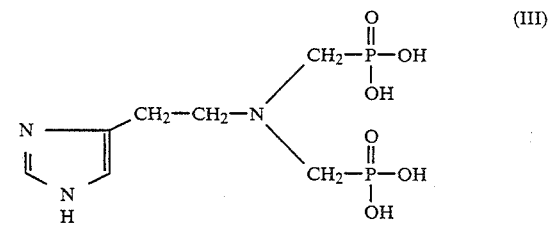

(III)

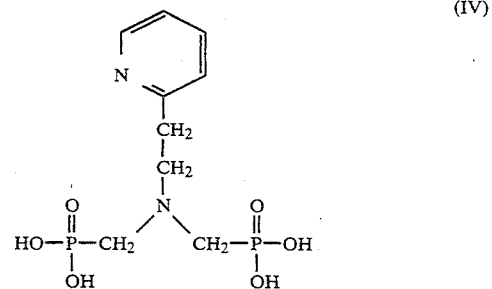

(IV)

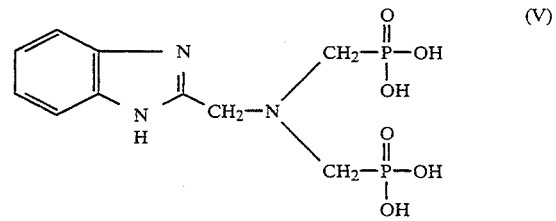

(V)

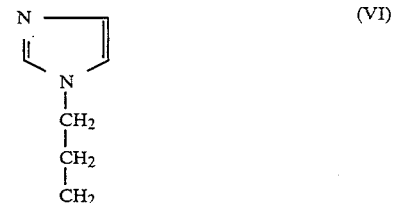

(VI)

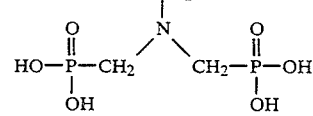

and

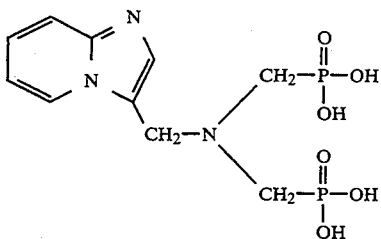

This invention further concerns a bone resorption inhibitor containing as an active ingredient the said heterocyclic iminobismethylenebisphosphonic acid derivative or an ester or salt thereof.

As the esters of the said bisphosphonic acid derivatives, there may be mentioned lower alkyl esters such as a methyl ester, an ethyl ester, a propyl ester or a butyl ester.

As the salts thereof, there may be mentioned alkali metal salts such as a sodium salt, a potassium salt, a barium salt or a lithium salt and an ammonium salt.

The present compounds can be prepared according to the process shown by the following reaction scheme:

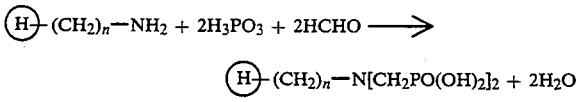

In this Mannich type reaction, the molar ratio of the starting materials is preferably of the ration of heterocyclic amine: phosphonic acid: formaldehyde = 1:2:2 and, when the starting materials are to be blended, it is preferable to add formaldehyde by bits the last thing. Reaction may be preferably carried out by heating under reflux to 60° C. or higher in an acidic solution, more preferably at 100±5° C. The reaction should be completed in several minutes to scores of hours.

The process of the reaction should be traced by thin layer chromatography (TLC). After the completion of the reaction, the reaction mixture should be preferably concentrated under reduced pressure and purified by cation exchange chromatography (solvent: water-hydrochloride). In case the reaction mixture is colored, it may be preferably treated with active carbon prior to cation exchange chromatography. After the completion of the purification, the resulting mixture may be again concentrated under reduced pressure and the residue may be recrystallized according to a conventional method (solvent: water-ethanol) to obtain the pure product.

The bone resorption inhibitory action of the heterocyclic iminobismethylenebisphosphonic acid derivatives of the present invention can be determined by examining the inhibitory effect of the above compounds with respect to the in vitro solubility of crystalline hydroxyapatite which is an important component of bone [Russell et. al., Calc. Tiss. Res., (1970), vol. 6, p. 183–196].

Where the present compounds are to be applied as a bone resorption inhibitor, they, as such, may be employed or in the form of a pharmaceutical preparation admixed with a pharmaceutically acceptable carrier well-known per se or a vehicle and others. One may apply any of oral administration with tablets, capsules, powders, granules, pills., syrups, and the like and parenteral administration with injections, ointments, suppositories and the like. These pharmaceutical preparations may be prepared according to a conventional method. A dose may vary depending upon the subject to be administered, the administration route to be applied, severity and others, and a suitable daily dose for adults is usually 0.1 mg–1 g in oral administration and 0.01–100 mg for parenteral.

In applying as a dental calculus formation inhibitory agent, the present compounds, as such, or salts thereof may be suitably incorporated into tooth paste, dental rinse, bad breath preventing agents, gargles and the like at the ratio by weight of 0.001–10%.

In applying as a polyvalent metal ion complex salt forming agent, the present compounds, as such, or salts thereof may be suitably incorporated into a metal ion solution depending upon the concentration of a metal ion.

This invention will be illustrated by way of the following Examples and Test Example.

Example 1

In 25 ml of water was dissolved 8.4 g of phosphorous acid, and, 5.4 g of 3-aminomethylpyridine and 25 ml of 35% hydrochloride were added successively thereto, then the resulting mixture was heated to 100(±5)° C. After heating, 10 ml of 37% formaldehyde was added to the mixture and then refluxed for 3 hours. After the reaction mixture was concentrated under reduced pressure, the residue was purified over cationic ion exchange chromatography and concentrated again under reduced pressure. The white solid thus obtained was recrystallized from water-ethanol to give 6.0 g of 3-opyridinylmethylimino-bismethylenebisphosphonic acid (II) as colorless crystals.

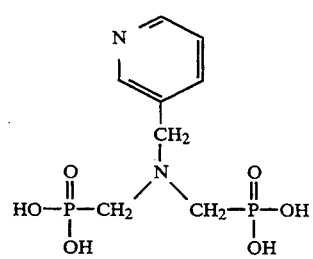

Physicochemical properties of the compound are as follows:

(I) Mass spectrometric value (m/z): FAB Mass 297 (M$^+$+1)

(11) Nuclear magnetic resonance spectra (D$_2$O, internal standard DSS)

d: 3.47, 3.61 (4H)
5.01 (2H)
8.15–8.31 (1H)
8.87–8.98 (2H)
9.16 (1H)

Example 2

The procedures in Example 1 were analogously repeated using 5.6 g of histamine to give 7.9 g of 2-(4- imidazolyl)ethyliminobismethylenebisphosphonic acid (III) as colorless crystals.

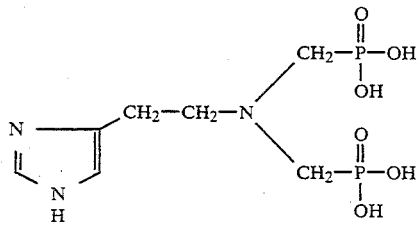

(I) Mass spectrometric value (m/z): FAB Mass $300(M^+ +1)$ (II) Nuclear magnetic resonance spectra ($D_2O$, internal standard DSS)
d: 3.27, 3.35, 3.45 (2H)
3.59, 3.73 (4H)
3.81, 3.91, 3.99 (2H)
7.44 (1H)
8.68 (1H)

Example 3

The procedures in Example 1 were analogously repeated using 6.1 g of (2-aminoethyl)pyridine to give 4.7 g of 2-(2-pyridinyl)ethyliminobismethylenebisphosphonic acid (IV) as colorless crystals.

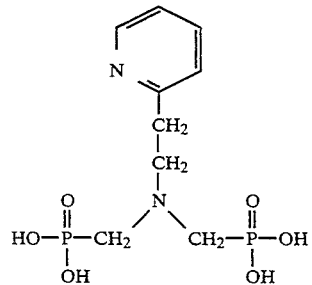

(I) Mass spectrometric value (m/z): FAB Mass $311(M^+ +1)$ (II) Nuclear magnetic resonance spectra ($D_2O$, internal standard DSS)
d: 3.67, 3.76 (4H)
3.30–4.04 (4H)
7.92–8.09 (2H)
8.49–8.77 (2H)

Example 4

The procedures in Example 1 were analogously repeated using 7.4 g of 2-(2-aminomethyl)benzimidazole to give 2.9 g of 3-benzimidazolylmethyliminobismethylenebisphosphonic acid (V) as colorless crystals.

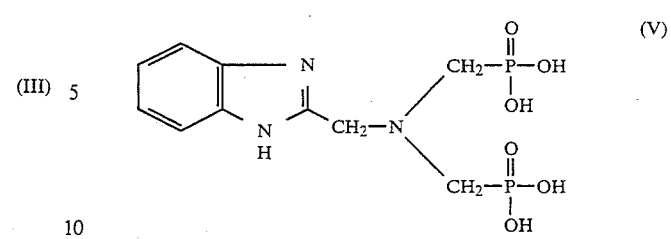

(I) Mass spectrometric value (m/z): FAB Mass $336(M^+ +1)$ (II) Nuclear magnetic resonance spectra ($D_2O$, internal standard DSS)
d: 3.14, 3.25 (4H)
4.63 (2H)
7.51, 7.55, 7.59, 7.62, 7.66, 7.69, 7.73, 7.77, 7.80, 7.83 (4H)

Example 5

The procedures in Example 1 were analogously repeated using 6.3 g of 1-(3-aminopropyl)imidazole to give 6.5 g of 3-(1-imidazolyl)propyliminobismethylenebisphosphonic acid (VI) as colorless crystals.

(I) Mass spectrometric value (m/z): FAB Mass $314(M^+ +1)$ (II) Nuclear magnetic resonance spectra ($D_2O$, internal standard DSS)
d: 2.30, 2.64 (2H)
3.53, 3.67 (4H)
3.59, 3.65, 3.72 (2H)
4.33, 4.41, 4.49 (2H)
7.50–7.58 (2H)
8.81 (1H)

Example 6

The procedures in Example 1 were analogously repeated using 7.35 g of 3-aminomethyl-imidazo [1,2-a]pyridine to give 6.5 g of 2-(imidazo[1,2-a]pyridyl-3-yl)methylbismethylenebisphosphonic acid (VII) as colorless crystals.

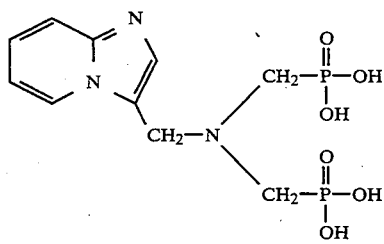

(VII)

(I) Mass spectrometric value (m/z): FAB Mass

336($M^+ + 1$)

Test Example

Hydroxyapatite adsorption test

Adsorption of the present iminobismethylenebisphosphonic acid derivatives to hydroxyapatite was tested based on Shinoda et. al.'s. method (Calclf. Tissue Int. (1983), vol. 35, p.87–99) with a slight modification in the following manner.

Namely, 65 mg of hydroxyapatite was suspended in 200 ml of 0.01 M barbital buffer (pH 7.0) containing 0.155M KCl, and the resulting suspension was stirred at 37° C. with a stirrer. After 24 hours of stirring, each agent to be tested was added to the equilibrated suspension in an amount of 0.075 mol per mol of hydroxyapatite, respectively, followed by another 2 hours' stirring. After the thus stirred suspension was filtered through meshes of 0.45 μm in diameter, the hydroxyapatite on the filter was scraped off and suspended again in 75 ml of the same barbital buffer as used above, followed by stirring at 37° C. with a stirrer. After 1 hour, the calcium concentration in the buffer was determined with an automatic calcium concentration analyzer (Hitachi Model 7050). From the calcium concentration determined after 1 hour, the inhibitory ability of each agent to be tested for the calcium dissociation through adsorption of the agent to hydroxyapatite was calculated. The determination was repeated three times for each agent.

The results are shown in Table 1. The t-test was performed, and the asterisked numerical values are of those compounds which showed a significant difference at 1%.

TABLE 1

| Compound | Calcium Concentration (mg/dl) |
|---|---|
| Control | 0.680 ± 0.006 |
| Compound (II) | 0.654 ± 0.006* |
| Compound (III) | 0.614 ± 0.012* |
| Compound (IV) | 0.630 ± 0.006* |
| Compound (V) | 0.530 ± 0.015* |

Average ± Standard deviation
*significant difference at 1%

As can be seen from Table 1, Compounds (II), (III), (IV) and (V) all inhibited significantly the calcium dissociation from hydroxyapatite. Particularly, Compounds (III) and (V) showed high inhibitory effect.

I claim:

1. A heterocyclic iminobismethylenebisphosphonic acid compound of the formula ( I ):

wherein n is an integer of 1 to 3 and the group of the formula

represents a pyridyl group, an imidazolyl group, a benzimidazolyl group ar an imidazol pyridyl group, or a pharmaceutically acceptable ester or salt thereof.

2. The heterocyclic iminobismethylenebisphosphonic acid compound of formula I according to claim 1, wherein the group of the formula

is a pyridyl group.

3. The heterocyclic iminobismethylenebisphosphonic acid compound of formula I according to claim 1, wherein the group of the formula

is an imidazolyl group.

4. The heterocyclic iminobismethylenebisphosphonic acid compound of formula I according to claim 1, wherein the group of the formula

is a benzimidazolyl group.

5. The heterocyclic iminobismethylenebisphosphonic acid compound of formula I according to claim 1, wherein the group of the formula

is an imidazo pyridyl group.

6. A pharmaceutical composition for inhibiting bone resorption comprising an effective amount of the heterocyclic iminobismethylenebisphosphonic acid compound of the formula (I) according to claim 1 in combination with a pharmaceutically acceptable carrier or vehicle.

7. A method of inhibiting bone resorption by administering an effective amount of a heterocyclic iminobismethylenebisphosphonic acid compound of the formula (I) according to claim 1 or a pharmaceutically acceptable ester or salt thereof.

8. A heterocyclic iminobismethylenebisphosphonic acid compound of the formula (I)

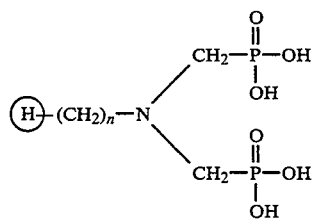

wherein n is an integer of 1 to 3 and the group of the formula

represents a pyridyl group, an imidazolyl group, benzimidazoiyl group or an imidazol[1,2-a]pyridyl group, or a pharmaceutically acceptable ester or salt thereof, and wherein said compound has one of the following chemical structures:

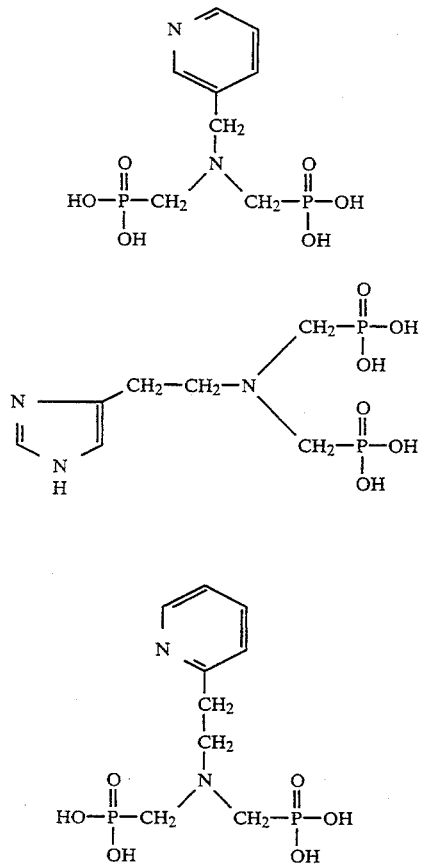

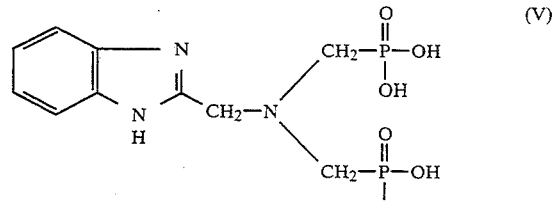

9. A pharmaceutical composition for inhibiting bone resorption comprising an effective amount of the heterocyclic iminobismethylenebisphosphonic acid compound of the formula (I) according to claim 8 in combination with a pharmaceutically acceptable carrier or a vehicle.

10. A method of inhibiting bone resorption by administering an effective amount of a heterocyclic iminobismethylenebisphosphonic acid compound of the formula (I) according to claim 8 or a pharmaceutically acceptable ester or salt thereof.

* * * * *

UNITED STATES PATENT AND TRADEMARK OFFICE
CERTIFICATE OF CORRECTION

PATENT NO. : 5,441,945
DATED : August 15, 1995
INVENTOR(S) : Katsuhiro YOSHIKAWA It is certified that error appears in the above-indentified patent and that said Letters Patent is hereby corrected as shown below:

CLAIM 1, COLUMN 8, LINE 1, "(H)-" SHOULD READ

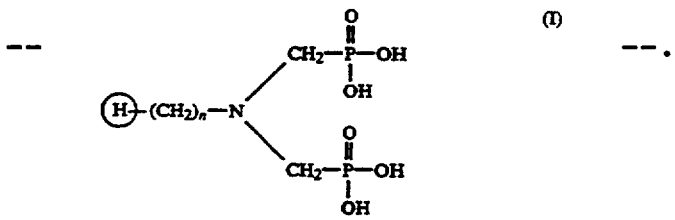

CLAIM 1, COLUMN 8, LINE 12, "ar" SHOULD READ --or--; AND "imidazol pyridyl" SHOULD READ --imidazol[1,2-a]pyridyl--.

IN THE SPECIFICATION, COLUMN 1, LINES 25-36, FORMULA(1)

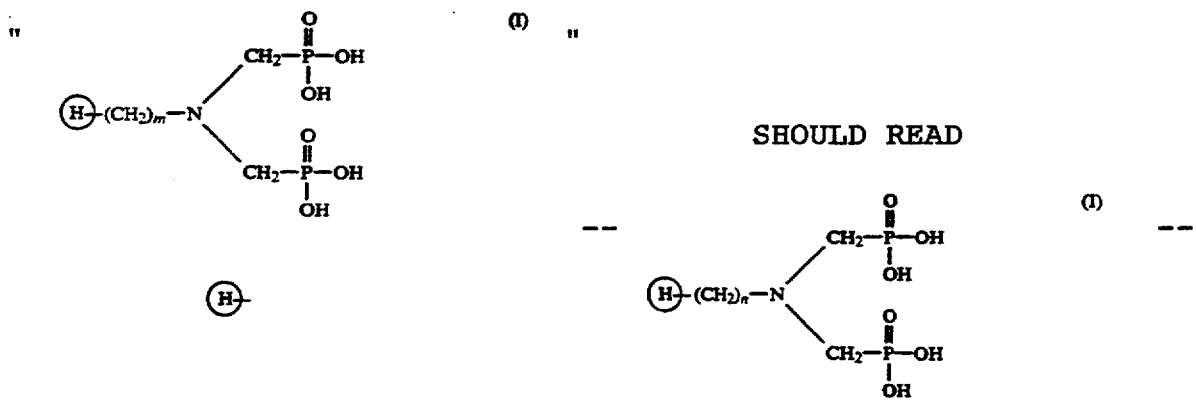

UNITED STATES PATENT AND TRADEMARK OFFICE
CERTIFICATE OF CORRECTION

PATENT NO. : 5,441,945
DATED : August 15, 1995
INVENTOR(S) : Katsuhiro YOSHIKAWA It is certified that error appears in the above-indentified patent and that said Letters Patent is hereby corrected as shown below:

IN THE SPECIFICATION, COLUMN 1, LINE 40, AFTER "formula", INSERT --  --.

Signed and Sealed this

Twenty-fourth Day of September, 1996

Attest:

BRUCE LEHMAN

Attesting Officer

Commissioner of Patents and Trademarks